(12) United States Patent
Bröcker et al.

(10) Patent No.: US 7,576,246 B1
(45) Date of Patent: Aug. 18, 2009

(54) ISOTHERMAL OPERATION OF HETEROGENEOUSLY CATALYZED THREE PHASE REACTIONS

(75) Inventors: Franz Josef Bröcker, Ludwigshafen (DE); Mathias Haake, Mannheim (DE); Gerd Kaibel, Lampertheim (DE); Gerd Rohrbacher, Ludwigshafen (DE); Ekkehard Schwab, Neustadt (DE); Manfred Stroezel, Ilvesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1434 days.

(21) Appl. No.: 09/629,482

(22) Filed: Jul. 31, 2000

(30) Foreign Application Priority Data

Aug. 2, 1999 (DE) ................. 199 36 276

(51) Int. Cl.
*C07C 5/10* (2006.01)
(52) U.S. Cl. .................. 585/266; 585/911; 585/914
(58) Field of Classification Search ......... 585/911, 585/914, 266
See application file for complete search history.

(56) References Cited

U.S. PATENT DOCUMENTS

| | | | |
|---|---|---|---|
| 4,227,021 A | 10/1980 | Grosskinsky et al. | |
| 4,514,520 A | 4/1985 | Uytterhoeven | 502/337 |
| 4,731,229 A | 3/1988 | Sperandio | 422/188 |
| 4,744,956 A | 5/1988 | Yant et al. | |
| 4,950,834 A * | 8/1990 | Arganbright et al. | 585/446 |
| 4,985,230 A | 1/1991 | Baden et al. | 423/650 |
| 5,773,670 A | 6/1998 | Gildert et al. | 585/266 |
| 5,939,589 A | 8/1999 | Kaibel et al. | 568/568 |
| 6,262,317 B1 | 7/2001 | Becker et al. | 568/861 |
| 6,297,415 B1 | 10/2001 | Brocker et al. | |
| 6,375,920 B2 * | 4/2002 | Fischer et al. | 423/584 |

FOREIGN PATENT DOCUMENTS

| | | |
|---|---|---|
| CA | 1146148 | 5/1983 |
| DE | 226872 | 7/1984 |
| GB | 1 416 194 | 12/1975 |
| JP | 48-63974 | 9/1973 |
| JP | 53-141212 A | 12/1978 |
| JP | 01-274835 | 11/1989 |
| JP | 06-345404 | 12/1994 |
| WO | 1997/48466 A1 | 12/1997 |
| WO | WO98/16463 * | 4/1998 |

OTHER PUBLICATIONS

*Ullmann's Enc. Ind. Chem.*, vol. B4, 1992, pp. 199-238.

* cited by examiner

*Primary Examiner*—Thuan Dinh Dang
(74) *Attorney, Agent, or Firm*—Novak Druce + Quigg LLP

(57) ABSTRACT

The invention relates to a process and apparatus for the isothermal operation of heterogeneously catalyzed reactions involving at least three phases in the form of a gaseous phase, a liquid phase and a solid phase. The invention provides apparatus for carrying out reactions involving a gaseous phase, a liquid phase and a solid phase, comprising (i) a dispersing element for dispersing a gas phase in a liquid phase to generate a reaction fluid, (ii) at least one reactor which possesses an inlet, an outlet and a reactor space bounded by heat-removing walls which are spaced apart substantially uniformly along the main flow axis of the reaction fluid, and which is fitted with catalyst-coated metal fabric, and (iii) a feed line which routes the reaction fluid from the dispersing element to the reactor inlet and is sufficiently short that the degree of dispersion of the reaction fluid does not substantially change in the course of the passage through the feed line.

6 Claims, 4 Drawing Sheets

ISOTHERMAL OPERATION OF HETEROGENEOUSLY CATALYZED THREE PHASE REACTIONS

This invention relates to a process and apparatus for the isothermal operation of heterogeneously catalyzed reactions involving at least three phases in the form of a gaseous phase, a liquid phase and a solid phase.

The invention relates specifically to the operation of such reactions where at least one reactant is liquid and one is gaseous and where the catalyst is a solid material.

The operation of such reactions is associated with appreciable difficulties. The gas-liquid transfer is frequently problematical. Moreover, isothermal conditions are difficult to achieve, isothermal being used in the sense that the heat of reaction is substantially evened out by input or removal of heat, so that temporal or local temperature fluctuations in the reactor are of no consequence.

Established processes are described in G. Eigenberger, Ullmann, 5th edition, vol. 4, p. 199ff. (1992) Wiley-VCH, Weinheim, Berlin, N.Y.

EP-B 0 305 203 (U.S. Pat. No. 4,985,230) describes the operation of heterogeneously catalyzed reactions under nonadiabatic conditions. To this end, a reactor with heat-transmitting walls is packed with monolithic catalysts. A monolithic catalyst is a coherent solid having a sufficiently large catalytic surface area that countable amounts of these bodies will suffice for catalyzing the reaction in question to an industrially sensible extent. The monolithic catalysts have channels which are angled relative to the overall flow direction, so that the reaction fluid is routed at an acute angle from one reactor wall to the other, which is said to improve the heat transfer. The shearing stress exerted on the reaction fluid is extremely high (high pressure drop) in reactor wall vicinity and otherwise rather low (poor mass transfer). This leads to unnecessarily large pressure drops in wall vicinity. The reactor is complicated to fabricate, since the pressure drop depends decisively on the geometry between reactor wall and monolithic catalyst.

EP-B 0 201 614 (U.S. Pat. No. 4,731,229) describes a reactor containing partly corrugated tape-form catalyst bodies whose corrugation is disposed at an inclination to the main flow axis and oppositely directed in adjacent plates, the pitch of the corrugation of the catalyst body being less than the pitch of the adjacent corrugated plates and the surface area of the catalyst body being larger than the surface area of an adjacent corrugated plate. This apparatus is not contemplated for generating gas-liquid dispersions. The complicated corrugation of the plates favors bypass formation, inhibits eddying and thus compromises mass transfer. In addition, the envisioned compact packing element does not provide for effective removal of the heat of reaction.

EP-B 0 068 862 (CA-A 1 146 148) discloses a fixed bed reactor for transfer reactions between gas phase and liquid. In this reactor, the fixed bed comprises alternating layers of plane and corrugated sheets coiled together to form a roll, the corrugated sheet comprising an open mesh material with at least an outer surface layer consisting of a high molecular weight organic polymeric substance which will be inherently hydrophobic with respect to the liquid mentioned, and the plane sheet comprising knitted, woven or felted cloth of a textile wicking material which is hydrophilic with respect to the liquid or the gas-liquid transfer reaction and which will provide an uninterrupted wicking path between the ends of the roll for the liquid mentioned. The disadvantage with this type of reactor is that the textile constituents of the reactor limit the cross-sectional flow velocities. The wicking path, moreover, inhibits rapid liquid transport, thus favors the separation between gas and liquid and inhibits the mass transfer between gas and liquid. Besides, the reactor is intended for adiabatic operation.

It is an object of the present invention to provide apparatus and a process for carrying out reactions involving a liquid phase, a gaseous phase and a solid phase with improved mass transfer between gas phase and liquid and with isothermal processing.

We have found that this object is achieved by apparatus for carrying out reactions involving a gaseous phase, a liquid phase and a solid phase, comprising
 a dispersing element for dispersing a gas phase in a liquid phase to generate a reaction fluid,
 at least one reactor which possesses an inlet, an outlet and a reactor space bounded by heat-removing walls which are spaced apart substantially uniformly along the main flow axis of the reaction fluid, and which is fitted with catalyst-coated metal fabric, and
 a feed line which routes the reaction fluid from the dispersing element to the reactor inlet and is sufficiently short that the degree of dispersion of the reaction fluid does not substantially change in the course of the passage through the feed line.

The inventors have determined that improved mass transfer can only be obtained if the reaction fluid is a dispersion formed from the gas phase (as disperse phase) and the liquid (as dispersion medium) and the process and apparatus are designed in such a way that the dispersion, as it passes through the reactor, remains stable, ie. substantially no increase in bubble size occurs.

The reactor of the invention is designed for maintaining a high but uniform shearing stress on the reaction fluid. On the one hand, it will withstand a high cross-sectional flow velocity without attrition of the catalyst. On the other, the reaction fluid is exposed to a uniformly high shearing stress in the metal fabric. This provides for uniform mixing of the reaction fluid and hence for a constant degree of dispersion of the reaction fluid as it passes through the reactor.

The catalyst-coated metal fabric of the invention is a woven or knitted metal fabric. The wire diameter is generally in the range from 0.01 to 5.0 mm, preferably from 0.04 to 1.0 mm. The mesh size may be varied within wide limits.

These wovens or knits may be coated by the process described in EP-B 0 564 830 (CA-A 2 090 930) or EP-A 0 965 384. EP-B 0 564 830 does not expressly describe the coating of metal knits with catalyst, but they shall be treated in the same way as woven metal fabrics. For the purposes of the present invention, knitted metal fabrics are metal fabrics formed from one continuous metal thread. Woven metal fabrics, in contrast, are fabrics formed from at least two metal threads.

The coating of woven or knitted metal fabrics with catalysts may also be effected by conventional dip processes, for example according to the process described in EP-A 0 056 435.

If the metal forming the woven or knitted metal fabric is itself catalytically active (possibly after a treatment), coating may be dispensed with entirely.

Woven or knitted metal fabrics may be used in the form of tapes. The catalyst-coated woven and knitted metal fabrics may be corrugated by means of a toothed wheel roll. The introduction of corrugated woven or knitted metal fabric in the reactor makes it possible to alter the packing density of the woven or knitted metal fabric. For instance, a plurality of layers of corrugated and smooth woven or knitted metal fabric may be introduced into the reactor space. Similarly, inert metal sheets may be inserted between layers of woven and knitted metal fabric. In any event, the catalyst-coated woven or knitted metal fabrics must be introduced in such a way that the reactor space is very uniformly packed between the heat-conducting walls. Uniform packing suppresses bypass formation and supports the conduction of heat to the heat-removing reactor walls, which in turn enable the reaction to be carried out under isothermal conditions.

In a further embodiment, the dispersing element is a liquid jet gas compressor. These conventional dispersing means are jet pumps for conveying and compressing gases.

In jet pumps, the jet of driving liquid breaks up into individual droplets on exit from the driving nozzle. These droplets become uniformly distributed across the cross section of the mixing nozzle, entrain ambient gas by impact and friction and compress it to a higher pressure. The attainable degree of dispersion is determined by the setting of driving nozzle and diffuser. This in turn depends on the pressure of the driving liquid, the suction pressure, the counterpressure, the flow of driving liquid, the gas suction stream and the mixture stream.

In a further embodiment of the apparatus according to the invention, the reactor is constructed as a heat exchanger. The transmission of heat through the reactor wall is decisively increased when a fluid medium on the reactor wall surface facing away from the reactor space takes up the heat of reaction and carries it away. Such a heat exchanger reactor can be constructed as a plate type heat exchanger or as a spiral type heat exchanger. A plate type heat exchanger reactor according to the invention has an in particular square or rectangular reactor space which is subdivided by additional heat-conducting walls which force the reaction fluid to take a zigzag course through the reactor space. Where the change of direction is greatest no catalyst-coated woven or knitted metal fabric is used in order that an excessively large pressure drop may be avoided. A spiral type heat exchanger reactor according to the invention has an in particular cylindrical reactor space which is packed very uniformly with catalyst-coated woven or knitted metal fabrics. The wall spacing of the heat exchanger reactors of the invention is preferably from 1 to 30 mm, especially from 2 to 20 mm, in particular from 4 to 10 mm.

The invention further provides a process for carrying out reactions involving a gaseous phase, a liquid phase and a solid phase, which comprises the steps of generating a reaction fluid by dispersing a gas phase in a liquid phase, passing the generated reaction fluid through a reactor whose reactor space is fitted with woven or knitted metal fabrics coated with catalyst, transferring the heat of reaction at the walls which bound the reactor space, and separating the reaction fluid into gas phase and liquid phase.

The separating of the reaction fluid may be effected using conventional separators.

The process is preferably carried out with the overall direction of flow of reaction fluid in the reactor being upward.

A further embodiment of the process according to the invention is operated with separate partial recycling of gas phase and/or liquid phase. By separate partial recycling is meant that the reaction product is separated from the gas phase and/or from the liquid phase. The remaining gas and the remaining liquid may be completely or partially redispersed and fed back to the reactor.

In a further embodiment of the process according to the invention, the superficial liquid velocity in the reactor is from 100 to 600 m$^3$/(m$^2$ h), preferably from 150 to 300 m$^3$/(m$^2$ h).

The superficial liquid velocity is the volume flow of the liquid fraction of the dispersion at the reaction conditions (pressure and temperature) divided by the cross-sectional area of the reactor space perpendicularly to the main flow axis. Since, as a result of woven or knitted metal fabrics being introduced, the reactor space is not available to the reaction fluid in its entirety, the actual microscopic superficial liquid velocity is correspondingly higher.

In a further embodiment of the process according to the invention, the superficial gas velocity is from 0.5 to 15 cm/s, preferably from 2.5 to 10 cm/s. The superficial gas velocity is herein defined similarly to the superficial liquid velocity.

In a further embodiment of the process according to the invention, the reaction fluid in the reactor is under a pressure of from 0.1 to 200 bar, preferably from 1 to 100 bar, especially from 1 to 10 bar.

In a further embodiment of the process according to the invention, the reaction fluid in the reactor has a temperature of from 25 to 250° C., preferably from 25 to 200° C., in particular from 50 to 150° C.

The invention will now be more particularly described with reference to FIGS. 1 to 4.

Figure 1:
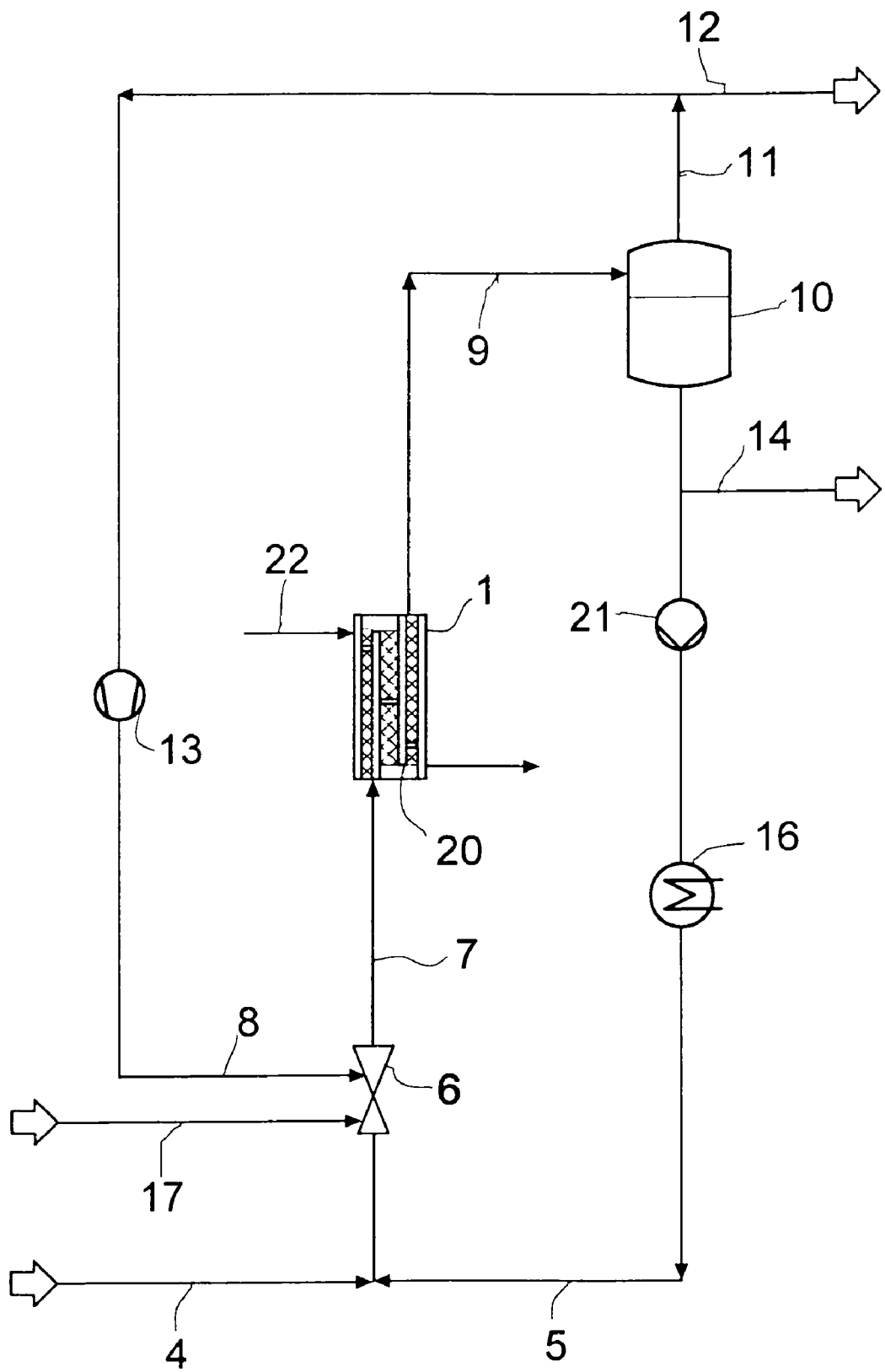
FIG. 1 shows an apparatus for a three phase reaction with product recycling, cycle gas operation using a liquid jet gas compressor and a plate type heat exchanger reactor.
Figure 2:
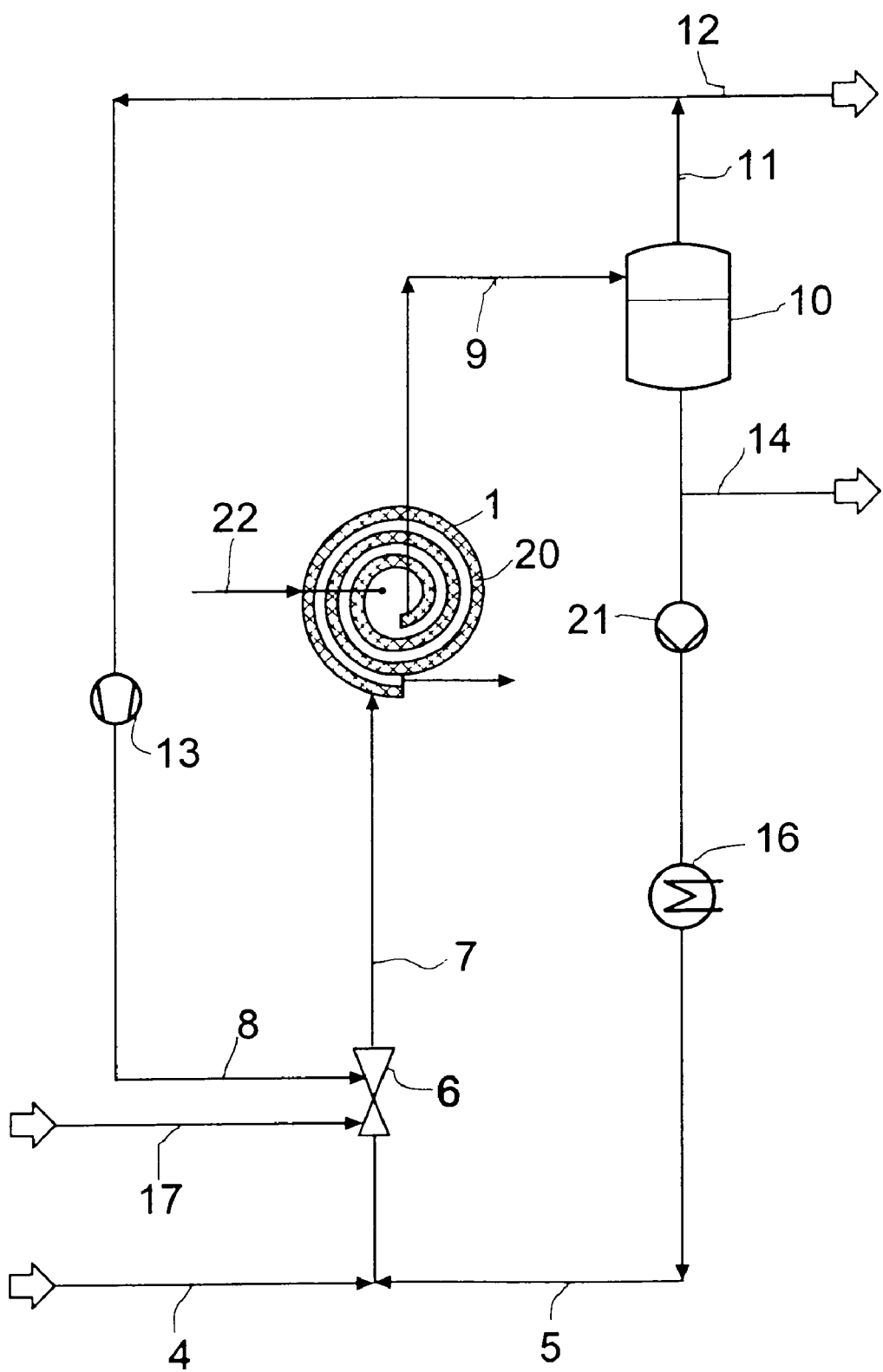
FIG. 2 shows an apparatus for a three phase reaction with product recycling, cycle gas operation using a liquid jet gas compressor and a spiral type heat exchanger reactor.

FIGS. 1 and 2 show an apparatus which, the metal fabric 20 supported catalyst in the reactor 1 having been activated (for example, by reduction with H$_2$), is filled with product liquid by using the circulating pump 21 to pump the liquid from the separator 10 via the optional preheater 16 and the feed line to the liquid jet gas compressor 5 to the liquid jet gas compressor 6 and from there to the heat exchanger reactor 1 and from it via the feed line to the separator 9 back into the separator 10. Cycle gas is withdrawn from the separator 10 via the feed line 11 and fed by means of the cycle gas pump 13 via the feed line to the liquid jet gas compressor 8 to the liquid jet gas compressor 6, where the gas is compressed and simultaneously dispersed in the liquid to form the reaction mixture. A sufficiently short feed line to reactor 7 such that the degree of dispersion of the reaction fluid does not substantially alter over this distance is used to feed the reaction fluid into the reactor 1. Once the circulation has been started up with product, the feed line to the liquid jet gas compressor 4 is used to introduce reactant, and a constant fill level system on the separator 10 is used to withdraw a corresponding amount of product from the liquid circulation via the discharge line 14. Fresh gas to replace the reaction gas consumed is fed into the gas circulation via the feed line to the liquid jet gas compressor 17, with the pressure being maintained, and off-gas is withdrawn from the gas circulation via the off-gas line 12. In the case of exothermic reactions the heat of reaction is removed from the reactor via the cooling circulation system 22, while in the case of endothermic reactions it is introduced.

Figure 3:
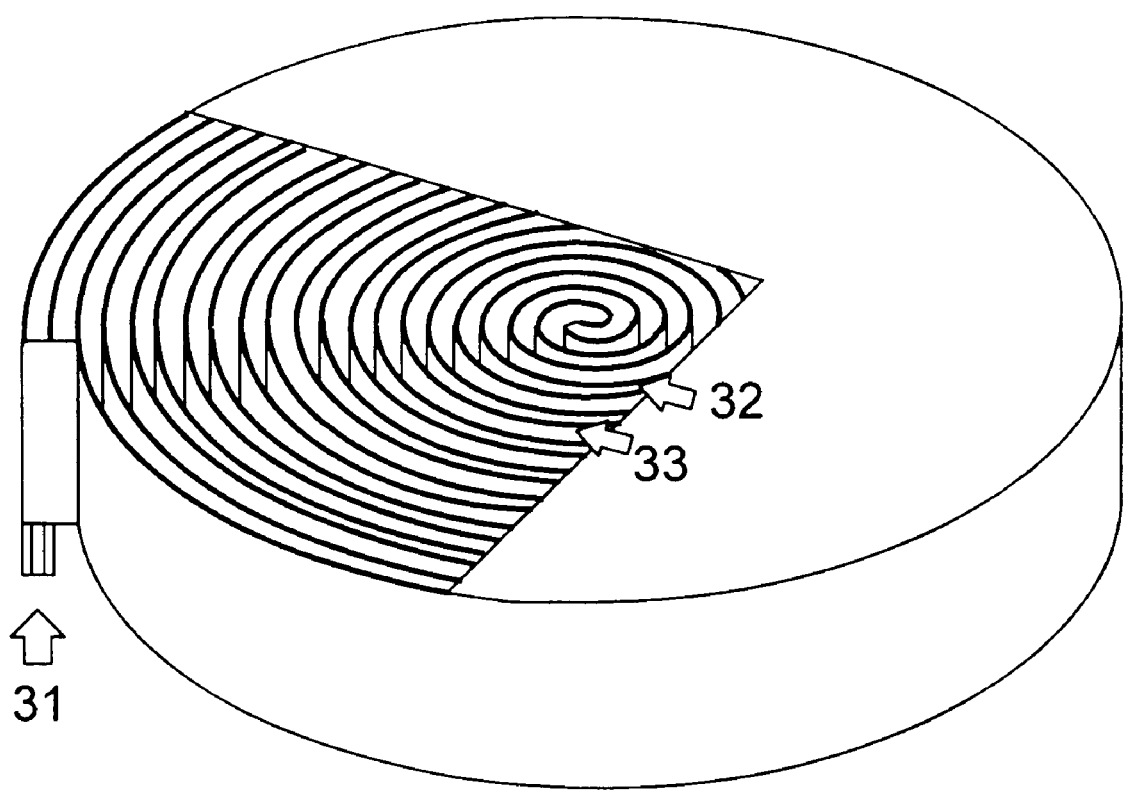
FIG. 3 shows a side view of the interior of a spiral type heat exchanger reactor.

FIG. 3 shows a side view of a spiral type heat exchanger reactor according to the invention. 31 identifies the feed for the reaction fluid into the reactor (reactor inlet). 32 identifies the reactor passage which will receive the catalyst-coated metal fabric, which will take up the entire space in more or less dense packing. 33 identifies the cooling passage, which is to receive the cooling fluid.

Figure 4:
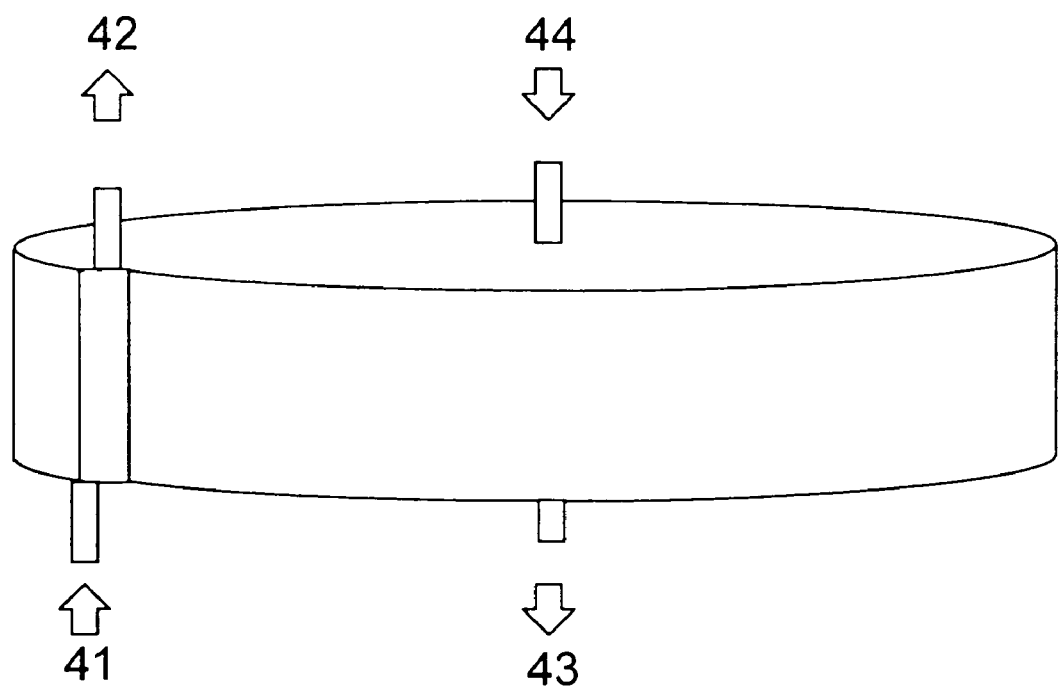
FIG. 4 shows a side view of a spiral type heat exchanger reactor.

FIG. 4 is a side view of a spiral type heat exchanger reactor and identifies the arrangement of the feed and discharge stubs. 41: reaction fluid feed (reactor inlet), 42: cooling fluid discharge, 43: reaction fluid discharge (reactor outlet), 44: cooling fluid feed. Reaction fluid and cooling fluid are here arranged in countercurrent in order that the heat transfer may be maximized. If the amount of heat released at the reactor inlet specifically is critical with regard to, for example, selectivity and catalyst stability, then a cocurrent arrangement is advisable.

The example hereinbelow illustrates the invention.

EXAMPLE

The hydrogenation of benzene to cyclohexane has an exotherm of $\Delta H = -214$ kJ/mol.

The benzene hydrogenation product equilibrates to between cyclohexane and methylcyclopentane, unless the heat of reaction is removed and a relatively low temperature is maintained.

Studies have also shown that the reaction is substrate-limited in that the low solubility of hydrogen in benzene and cyclohexane causes the reaction mixture to deplete in dissolved $H_2$ along the catalyst layer. It is therefore advantageous to use the invention to improve the supply of dissolved hydrogen.

The benzene hydrogenation process is carried out using an inventive apparatus as per FIG. 2, comprising a spiral type heat exchanger reactor as per FIGS. 3 and 4. To this end, the reactor passage 5 mm in width, 25 mm in depth and 960 mm in length (volume 120 ml) was packed with 8 plies of knitted catalyst fabric tape prepared by first heat-treating a knitted support tape of V2A stainless steel (German material number 1.4301) at 650° C. for 3 h and then vacuum-coating it with 6 nm of platinum. The amount of active component was 46 mg. The catalyst-packed heat exchanger reactor was installed in the apparatus depicted in FIG. 3. After purging with nitrogen and reduction of the catalyst with hydrogen at 80° C. for 2 h, benzene was pumped via the feed line 4 into the cyclohexane-filled liquid circulation system. The reaction parameters were p=20 bar, T=90° C. and a superficial liquid and hydrogen velocity of 400 $m^3/m^2h$.

The temperature of the reaction product was measured at the reactor outlet. A maximum temperature difference of 0.2° C. was observed relative to the reaction temperature setting.

A selectivity of 100% was obtained with 98% conversion. The space-time yield based on the volume of the reactor passage was 0.5 kg/(l·h).

We claim:

1. A process for carrying out a reaction under isothermal conditions involving a gas phase, containing at least one gaseous reactant, a liquid phase containing at least one liquid reactant and a solid phase which is a catalyst, which comprises the steps of generating a reaction fluid by dispersing the gas phase containing the at least one gaseous reactant in the liquid phase, containing the at least one liquid reactant and producing a reaction thereby, passing the generated reaction fluid, without substantial change in the degree of the dispersion of said reaction fluid, through a reactor whose reactor space is equipped with woven or knitted metal fabrics coated with catalyst transferring the heat through the reactor to a cooling fluid medium on the reaction wall surface facing away the reactor space, and separating the reaction fluid into gas phase and liquid-phase.

2. A process as claimed in claim 1, operated with separate partial recycling of gas phase and/or liquid phase.

3. A process as claimed in claim 1, wherein the superficial liquid velocity in the reactor is from 100 to 66 $m^3.m^2h$).

4. A process as claimed in claim 1, wherein the superficial gas velocity from 0.5 to 15 cm/s.

5. A process as claimed in claim 1, wherein the reaction fluid in the reactor is under a pressure of from 0.1 to 200 bar.

6. A process as claimed in claim 1, wherein the reaction fluid in the reactor has a temperature of from 25 to 250° C.

* * * * *